United States Patent
Yoshida

(10) Patent No.: US 8,121,369 B2
(45) Date of Patent: Feb. 21, 2012

(54) MEDICAL IMAGE PROCESSING APPARATUS AND MEDICAL IMAGE PROCESSING METHOD

(75) Inventor: Ryoko Yoshida, Nasushiobara (JP)

(73) Assignee: Olympus Medical Systems Corp., Tokyo (JP)

(*) Notice: Subject to any disclaimer, the term of this patent is extended or adjusted under 35 U.S.C. 154(b) by 236 days.

(21) Appl. No.: 12/652,321

(22) Filed: Jan. 5, 2010

(65) Prior Publication Data

US 2010/0104156 A1 Apr. 29, 2010

Related U.S. Application Data

(63) Continuation of application No. PCT/JP2008/056947, filed on Apr. 8, 2008.

(30) Foreign Application Priority Data

Jul. 26, 2007 (JP) .................................. 2007-194987

(51) Int. Cl.
G06K 9/00 (2006.01)

(52) U.S. Cl. ......... 382/128; 382/131; 382/133; 382/203

(58) Field of Classification Search .................. 382/128, 382/130, 132, 203, 131, 133; 600/407, 431, 600/476, 160; 348/65, 68
See application file for complete search history.

(56) References Cited

U.S. PATENT DOCUMENTS

| | | | |
|---|---|---|---|
| 6,366,800 B1* | 4/2002 | Vining et al. | 600/425 |
| 7,379,572 B2* | 5/2008 | Yoshida et al. | 382/128 |
| 7,953,261 B2* | 5/2011 | Nishimura et al. | 382/128 |
| 2003/0048931 A1* | 3/2003 | Johnson et al. | 382/128 |
| 2003/0223627 A1 | 12/2003 | Yoshida et al. | |
| 2006/0114796 A1* | 6/2006 | Maruyama et al. | 369/112.01 |
| 2009/0079737 A1* | 3/2009 | Inoue et al. | 345/424 |

FOREIGN PATENT DOCUMENTS

| | | |
|---|---|---|
| JP | 11-337845 | 12/1999 |
| JP | 2001-513923 | 9/2001 |
| JP | 2006-061274 | 3/2006 |
| WO | WO2005/084520 | * 3/2004 |

OTHER PUBLICATIONS

Abstract of corresponding International Publication No. WO 98/37517, dated Aug. 27, 1998.
International Search Report dated Jul. 15, 2008.

* cited by examiner

Primary Examiner — Daniel Mariam
Assistant Examiner — Nancy Bitar
(74) Attorney, Agent, or Firm — Scully, Scott, Murphy & Presser, P.C.

(57) ABSTRACT

The medical image processing apparatus of the present invention includes: a three-dimensional model estimating section that estimates a three-dimensional model based on a two-dimensional image; a local region setting section that sets a plurality of local regions around a target pixel in the two-dimensional image; a shape feature value calculating section that uses three-dimensional coordinate data corresponding to the plurality of local regions and calculates shape feature values of respective voxels corresponding to the target pixel; a shape feature value selecting section that selects, as a shape feature value of a voxel corresponding to the target pixel, a shape feature value calculated according to one local region including an optimum three-dimensional coordinate data amount among the plurality of shape feature values; and an elevated shape detecting section that detects an elevated shape existing in the two-dimensional image based on a selection result of the shape feature value selecting section.

14 Claims, 5 Drawing Sheets

MEDICAL IMAGE PROCESSING APPARATUS AND MEDICAL IMAGE PROCESSING METHOD

CROSS REFERENCE TO RELATED APPLICATION

This application is a continuation application of PCT/JP2008/056947 filed on Apr. 8, 2008 and claims benefit of Japanese Application No. 2007-194987 filed in Japan on Jul. 26, 2007, the entire contents of which are incorporated herein by this reference.

BACKGROUND OF THE INVENTION

1. Field of the Invention

The present invention relates to a medical image processing apparatus and a medical image processing method, and more particularly to a medical image processing apparatus and a medical image processing method that detects a lesion having an elevated shape existing in a two-dimensional image of an image of living tissue based on the two-dimensional image.

2. Description of the Related Art

An endoscope system including an endoscope and a medical image processing apparatus or the like is widely used in the medical field. Specifically, the endoscope system includes, for example, the endoscope including an insertion portion inserted into a body cavity as a living body, an objective optical system placed in a distal end portion of the insertion portion, and an image pickup portion that picks up an image of the inside of the body cavity formed by the objective optical system and outputs the image as an image pickup signal, and the medical image processing apparatus that performs a process for displaying the image of the inside of the body cavity on a monitor or the like as a display portion based on the image pickup signal. Then, based on the image of the inside of the body cavity displayed on the monitor or the like as the display portion, a user observes, for example, an organ or the like as a subject in the body cavity.

Also, the endoscope system including the above-described configuration can also pick up an image of, for example, mucosa of a digestive tract such as a large intestine as a subject in the body cavity. Thus, the user can comprehensively observe, for example, various comprehensive findings such as a color tone of the mucosa, a shape of a lesion, and a microstructure of a mucosa surface.

Further, in recent years, an endoscope apparatus has been proposed that can produce a three-dimensional model of a subject based on data of a two-dimensional image according to an image pickup signal of an image of the subject picked up by an endoscope.

Meanwhile, as a method for identifying a lesion having an elevated shape such as a polyp in a three-dimensional model produced by, for example, CT (Computed Tomography), a method is proposed that can identify the lesion by evaluating a shape of the three-dimensional model based on a shape feature value such as ShapeIndex or Curvedness as described in US Patent Application Publication No. 20030223627.

SUMMARY OF THE INVENTION

The medical image processing apparatus of the present invention includes: a three-dimensional model estimating section that estimates a three-dimensional model of living tissue based on a two-dimensional image of an image of the living tissue inputted from a medical image pickup apparatus; a local region setting section that sets a plurality of local regions around a target pixel in the two-dimensional image; a shape feature value calculating section that uses three-dimensional coordinate data corresponding to each of the plurality of local regions and calculates shape feature values of respective voxels corresponding to the target pixel based on the three-dimensional model of the living tissue estimated by the three-dimensional model estimating section; a shape feature value selecting section that selects, as an optimum shape feature value of a voxel corresponding to the target pixel, a shape feature value calculated according to one local region including an optimum three-dimensional coordinate data amount among the plurality of shape feature values calculated according to the plurality of local regions; and an elevated shape detecting section that detects an elevated shape existing in the two-dimensional image based on a selection result of the shape feature value selecting section.

A medical image processing method of the present invention includes steps of: estimating a three-dimensional model of living tissue based on a two-dimensional image of an image of the living tissue inputted from a medical image pickup apparatus; setting a plurality of local regions around a target pixel in the two-dimensional image; using three-dimensional coordinate data corresponding to each of the plurality of local regions and calculating shape feature values of respective voxels corresponding to the target pixel based on the three-dimensional model of the living tissue; selecting, as an optimum shape feature value of a voxel corresponding to the target pixel, a shape feature value calculated according to one local region including an optimum three-dimensional coordinate data amount among the plurality of shape feature values calculated according to the plurality of local regions; and detecting an elevated shape existing in the two-dimensional image based on a result of the selection.

DETAILED DESCRIPTION OF THE PREFERRED EMBODIMENT(S)

Now, an embodiment of the present invention will be described with reference to the drawings.

Figure 1:
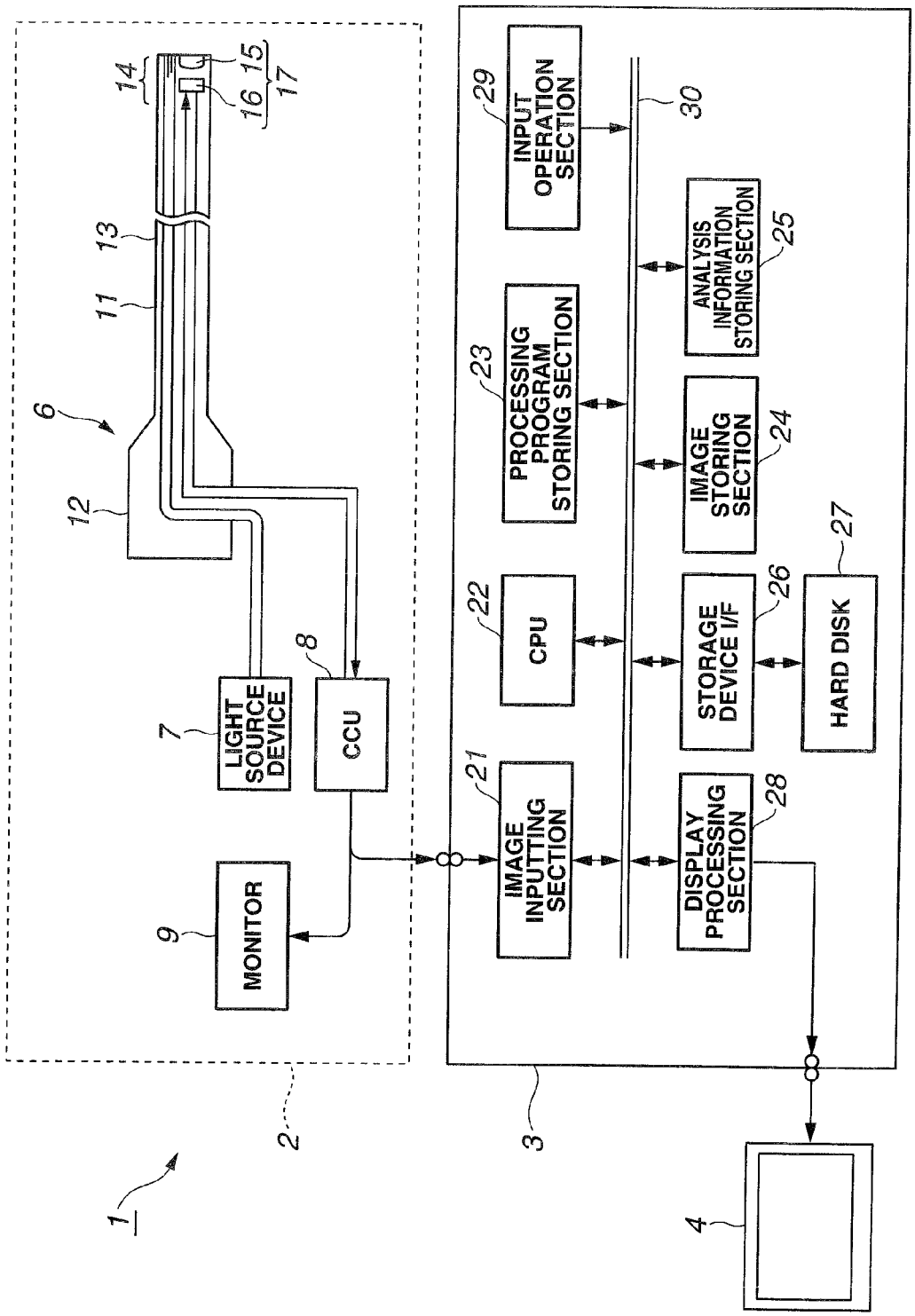
FIG. 1 is a diagram of an example of a configuration of essential parts in an endoscope system in which a medical image processing apparatus according to an embodiment of the present invention is used.
Figure 2:
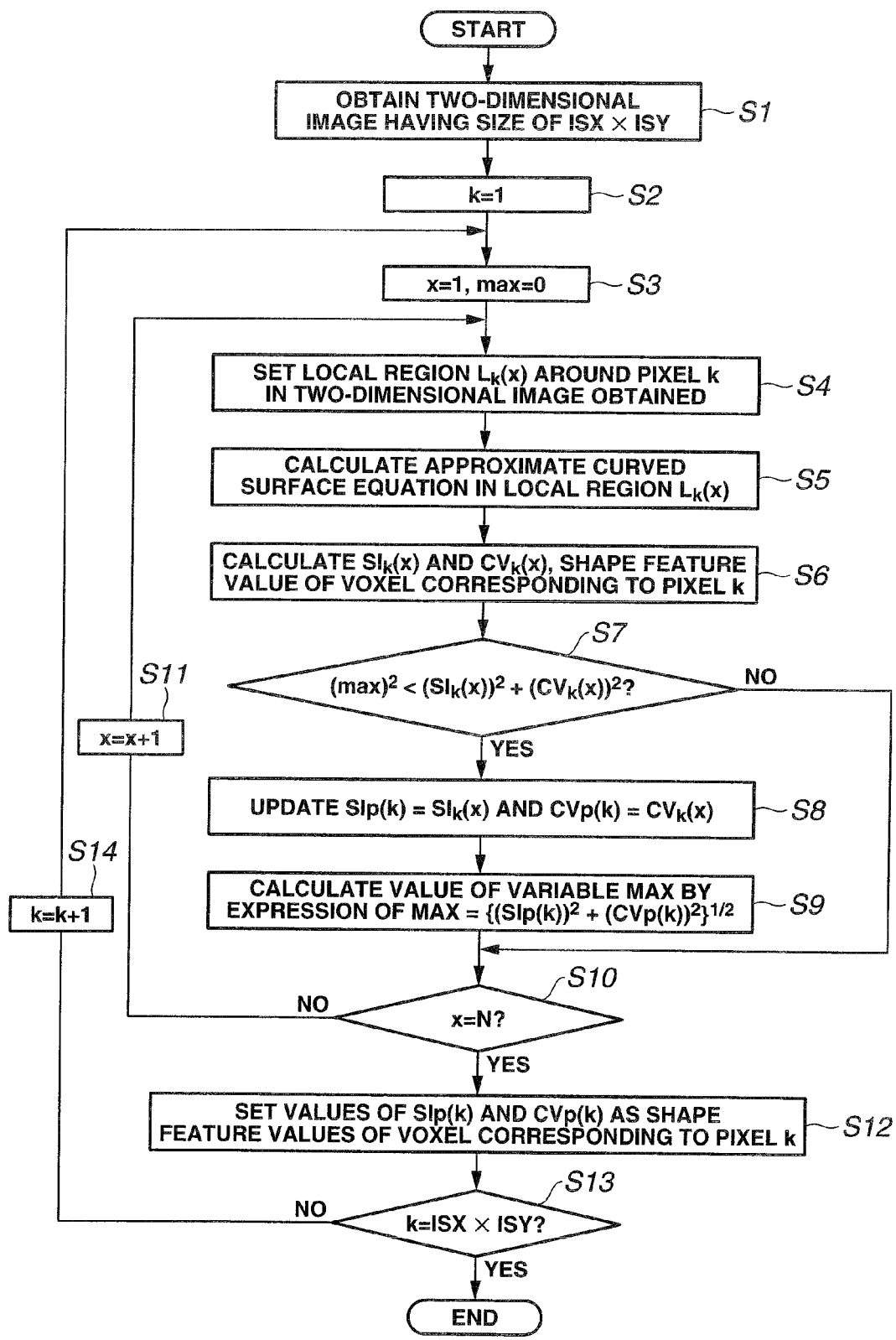
FIG. 2 is a flowchart of an example of a process performed in the medical image processing apparatus in FIG. 1.
Figure 3:
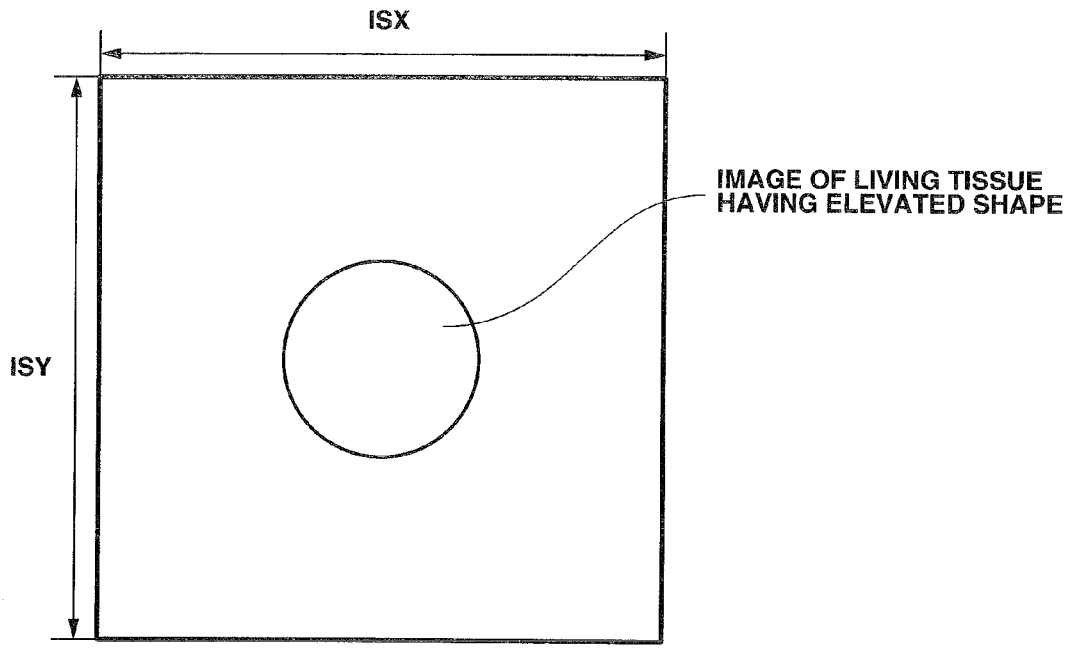
FIG. 3 is a diagram of an example of a two-dimensional image subjected to the process shown in FIG. 2.
Figure 4:
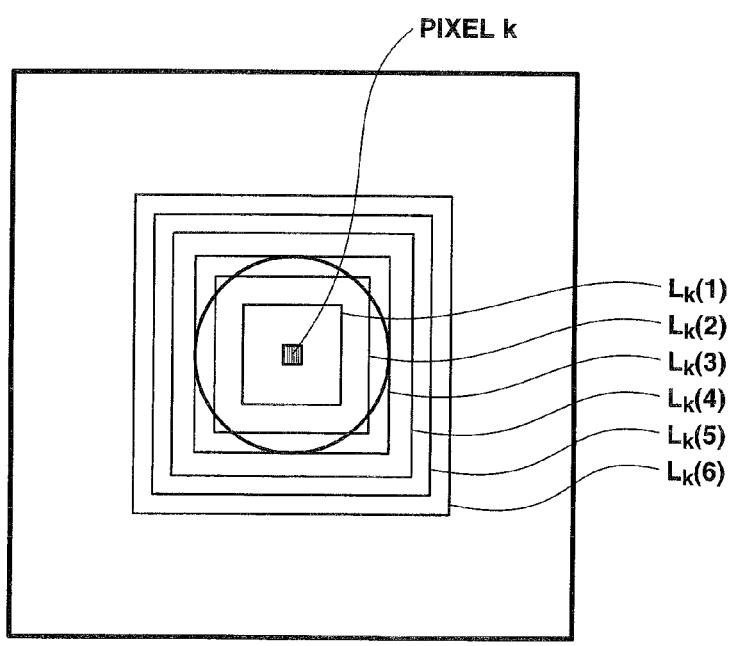
FIG. 4 is a diagram of an example of each local region applied for calculating a shape feature value of one pixel in the process shown in FIG. 2.
Figure 5:
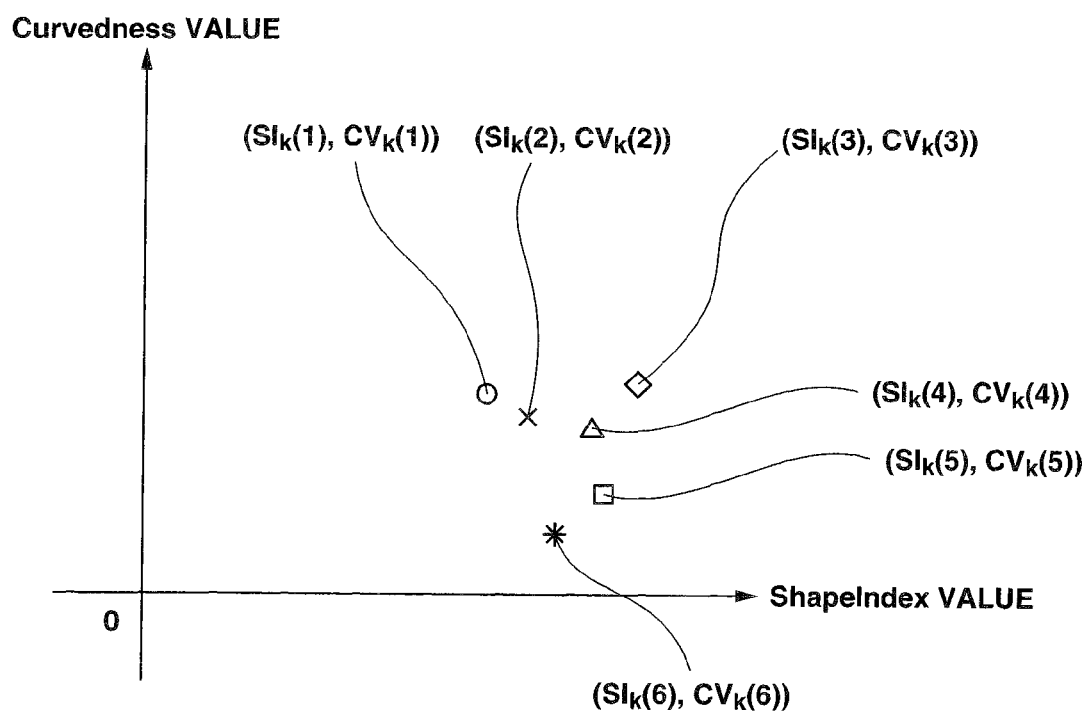
FIG. 5 is a scatter diagram showing distribution of shape feature values of one pixel calculated by the process shown in FIG. 2.
Figure 6:
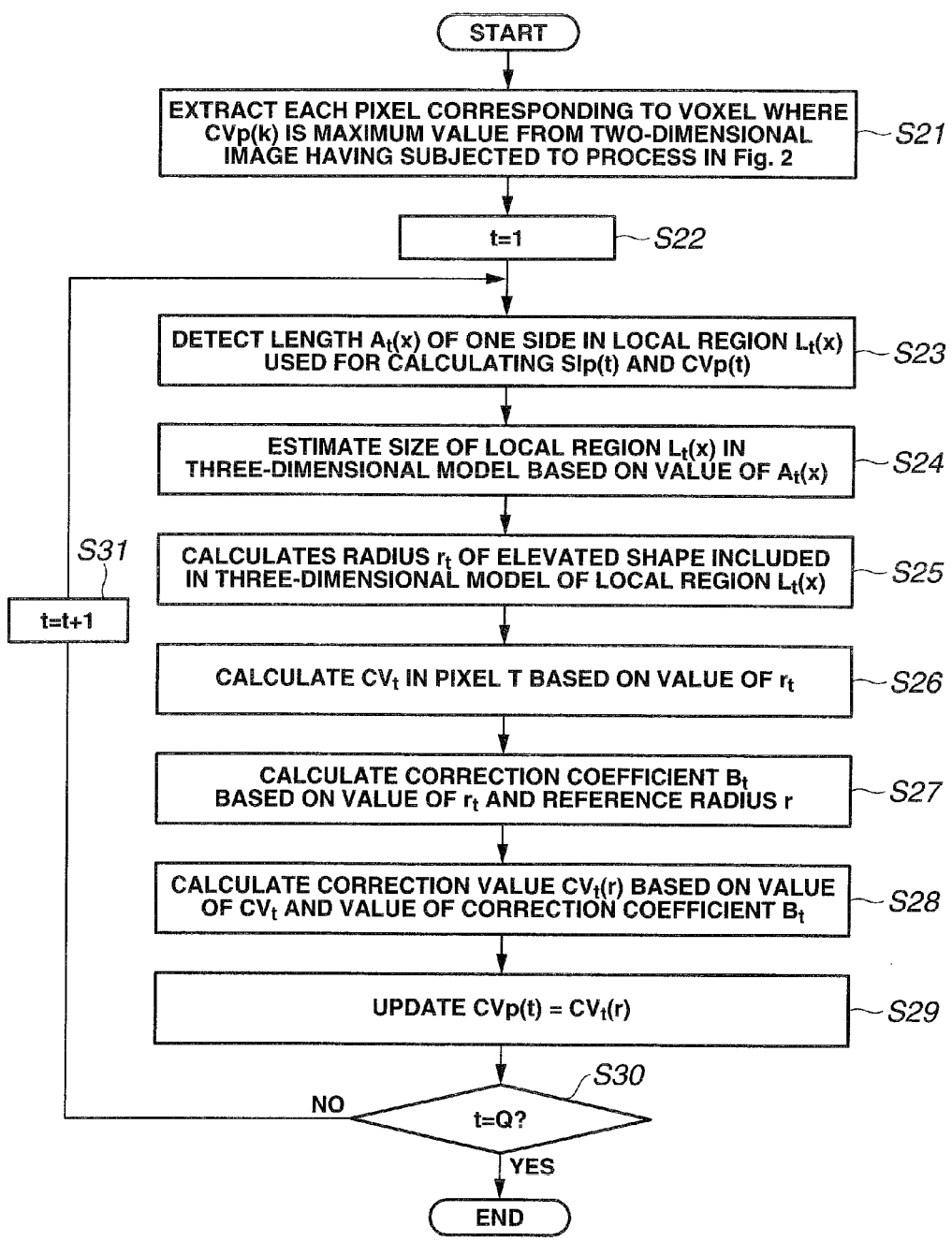
FIG. 6 is a flowchart of an example of a process performed after the process shown in FIG. 2 in the medical image processing apparatus in FIG. 1.

FIGS. 1 to 6 relate to an embodiment of the present invention. FIG. 1 is a diagram of an example of a configuration of essential parts in an endoscope system in which a medical image processing apparatus according to an embodiment of the present invention is used. FIG. 2 is a flowchart of an example of a process performed in the medical image processing apparatus in FIG. 1. FIG. 3 is a diagram of an example of a two-dimensional image subjected to the process shown in FIG. 2. FIG. 4 is a diagram of an example of each local region applied for calculating a shape feature value of one pixel in the process shown in FIG. 2. FIG. 5 is a scatter diagram showing distribution of shape feature values of one pixel calculated by the process shown in FIG. 2. FIG. 6 is a flowchart of an example of a process performed after the process shown in FIG. 2 in the medical image processing apparatus in FIG. 1.

As shown in FIG. 1, an endoscope system 1 includes, as essential parts, a medical observation device 2 that picks up an image of a subject and outputs a two-dimensional image of the image of the subject, a medical image processing apparatus 3 that is constituted by a personal computer or the like, performs image processing of a video signal of the two-dimensional image outputted from the medical observation device 2 and outputs the video signal having subjected to the image processing as an image signal, and a monitor 4 that displays an image based on the image signal outputted from the medical image processing apparatus 3.

The medical observation device 2 includes, as essential parts, an endoscope 6 that is inserted into a body cavity, picks up an image of a subject in the body cavity, and outputs the image as an image pickup signal, a light source device 7 that supplies an illumination light for illuminating the subject whose image is picked up by the endoscope 6, a camera control unit (hereinafter abbreviated as CCU) 8 that performs various controls of the endoscope 6, performs signal processing of the image pickup signal outputted from the endoscope 6, and outputs the signal as a video signal of the two-dimensional image, and a monitor 9 that displays the image of the subject picked up by the endoscope 6 based on the video signal of the two-dimensional image outputted from the CCU 8.

The endoscope 6 includes an insertion portion 11 inserted into the body cavity, and an operation portion 12 provided on a proximal end side of the insertion portion 11. A light guide 13 for transmitting the illumination light supplied by the light source device 7 is inserted through a portion from the proximal end side in the insertion portion 11 to a distal end portion 14 on a distal end side in the insertion portion 11.

A distal end side of the light guide 13 is placed in the distal end portion 14 of the endoscope 6, and a rear end side thereof is connected to the light source device 7. Since the light guide 13 has such a configuration, the illumination light supplied by the light source device 7 is transmitted by the light guide 13 and then emitted from an unshown illumination window provided on a distal end surface of the distal end portion 14 of the insertion portion 11. Then, the illumination light is outputted from the unshown illumination window to illuminate living tissue or the like as the subject.

In the distal end portion 14 of the endoscope 6, an objective optical system 15 mounted to an unshown observation window adjacent to the unshown illumination window, and an image pickup portion 17 that is placed in an image forming position of the objective optical system 15 and has an image pickup device 16 constituted by, for example, a CCD (charge-coupled device) are provided. With such a configuration, the image of the subject formed by the objective optical system 15 is picked up by the image pickup device 16 and then outputted as the image pickup signal.

The image pickup device 16 is connected to the CCU 8 via a signal wire. Then, the image pickup device 16 is driven based on a drive signal outputted from the CCU 8, and also outputs the image pickup signal to the CCU 8.

Also, the image pickup signal inputted to the CCU 8 is subjected to the signal processing in an unshown signal processing circuit provided in the CCU 8, and thus converted and outputted as the video signal of the two-dimensional image. The video signal of the two-dimensional image outputted from the CCU 8 is outputted to the monitor 9 and the medical image processing apparatus 3. Thus, the image of the subject based on the video signal outputted from the CCU 8 is displayed as the two-dimensional image on the monitor 9.

The medical image processing apparatus 3 includes an image inputting section 21 that performs A/D conversion of the video signal of the two-dimensional image outputted from the medical observation device 2 and outputs the video signal, a CPU 22 as a central processing unit that performs the image processing of the video signal outputted from the image inputting section 21, a processing program storing section 23 in which a processing program related to the image processing has been written, an image storing section 24 that stores the video signal outputted from the image inputting section 21 or the like, and an analysis information storing section 25 that stores image data or the like as an image processing result of the CPU 22.

Also, the medical image processing apparatus 3 includes a storage device interface 26, a hard disk 27 as a storage device that stores image data or the like as the image processing result of the CPU 22 via the storage device interface 26, a display processing section 28 that performs display processing for displaying the image data on the monitor 4 based on the image data as the image processing result of the CPU 22, and also outputs the image data having been subjected to the display processing as an image signal, and an input operation section 29 constituted by a keyboard or the like with which a user can input parameters in the image processing performed by the CPU 22 and operation instructions to the medical image processing apparatus 3. The monitor 4 displays the image based on the image signal outputted from the display processing section 28.

The image inputting section 21, the CPU 22, the processing program storing section 23, the image storing section 24, the analysis information storing section 25, the storage device interface 26, the display processing section 28, and the input operation section 29 in the medical image processing apparatus 3 are connected to one another via a data bus 30.

Next, an operation of the endoscope system 1 will be described.

First, the user inserts the insertion portion 11 of the endoscope 6 into a tubular organ such as a large intestine, for example. Then, when the insertion portion 11 is inserted into the tubular organ by the user, an image of living tissue existing on an inner wall of the tubular organ and having an elevated shape is picked up by the image pickup portion 17 provided in the distal end portion 14. Then, the image of the living tissue having the elevated shape is outputted as the image pickup signal from the image pickup portion 17 to the CCU 8.

The CCU 8 performs the signal processing of the image pickup signal outputted from the image pickup device 16 of the image pickup portion 17 in the unshown signal processing circuit, and thus converts the image pickup signal into the video signal of the two-dimensional image and outputs the video signal. Then, the monitor 9 displays, as the two-dimensional image, the image of the living tissue having the elevated shape based on the video signal outputted from the CCU 8. Also, the CCU 8 outputs the video signal of the two-dimensional image obtained by performing the signal processing of the image pickup signal outputted from the image pickup device 16 of the image pickup portion 17, to the medical image processing apparatus 3.

The video signal of the two-dimensional image outputted to the medical image processing apparatus 3 is A/D converted in the image inputting section 21, and then inputted to the CPU 22.

Then, the CPU 22 having a function as a three-dimensional model estimating section performs a process such as geometric conversion, for example, based on luminance information or the like of the video signal of the two-dimensional image outputted from the image inputting section 21, and estimates a three-dimensional model of the living tissue having the elevated shape (obtains three-dimensional coordinate data). Specifically, the CPU 22 corrects distortion of the video signal of the two-dimensional image outputted from the image inputting section 21, caused by image surface curving of the objective optical system 15, and then applies, for example, an image processing method described in Japanese Patent Application Laid-Open Publication No. 11-337845 to an R (red) component contained in the video signal to estimate a three-dimensional model of the living tissue having the elevated shape (obtains three-dimensional coordinate data).

Next, a process for calculating a shape feature value based on the three-dimensional model (three-dimensional coordinate data) of the living tissue having the elevated shape will be described.

First, the CPU 22 obtains a two-dimensional image having a size of ISX×ISY (for example, 45×45) as a two-dimensional image including an image of living tissue having an elevated shape as shown in FIG. 3 (Step S1 in FIG. 2). The image of the living tissue having the elevated shape included in the image shown in FIG. 3 is an image picked up from an upper side of the elevated shape.

Then, the CPU 22 having a function as a local region setting section sets a value of a pixel k ($1 \leq k \leq ISX \times ISY$) as a target pixel to 1 (Step S2 in FIG. 2), sets a value of a variable x ($1 \leq x \leq N$) to 1, and sets a value of a variable max to 0 (Step S3 in FIG. 2), and then sets a local region $L_k(x)$ around the pixel k in the two-dimensional image obtained by the process in Step S1 in FIG. 2 (Step S4 in FIG. 2). In the present embodiment, the local region $L_k(x)$ is a region having a length of one side of $A_k(x)$ (having a size of $A_k(x) \times A_k(x)$).

Then, the CPU 22 calculates an approximate curved surface equation in the local region $L_k(x)$ based on three-dimensional coordinate data corresponding to each two-dimensional coordinate in the local region $L_k(x)$ among the previously obtained three-dimensional coordinate data (Step S5 in FIG. 2). Then, the CPU 22 having a function as a shape feature value calculating section calculates a ShapeIndex value $SI_k(x)$ and a Curvedness value $CV_k(x)$ as a shape feature value of a voxel corresponding to the pixel k based on the calculated approximate curved surface equation (Step S6 in FIG. 2).

The above-described ShapeIndex value is a value for indicating a concave or convex state of each voxel in a three-dimensional model, and indicated as a numerical value within a range of 0 to 1. Specifically, in one voxel (or one voxel group) existing in the three-dimensional model, when the ShapeIndex value is close to 0, the existence of a concave shape is indicated, and when the ShapeIndex value is close to 1, the existence of a convex shape is indicated. The above-described Curvedness value is a value corresponding to a curvature of each voxel in the three-dimensional model. Specifically, in one voxel (or one voxel group) existing in the three-dimensional model, when the Curvedness value is smaller, the existence of a more gently curved surface is indicated, and when the Curvedness value is larger, the existence of a more sharply curved surface is indicated. Further, the ShapeIndex value and the Curvedness value can be calculated by the same method as described in, for example, US Patent Application No. 20030223627. Thus, in the present embodiment, a description of a specific calculating method of the ShapeIndex value and the Curvedness value in one voxel (or one voxel group) will be omitted.

The CPU 22 determines whether values of the variable max, the ShapeIndex value $SI_k(x)$, and the Curvedness value $CV_k(x)$ satisfy the relationship in the following Expression (1) (Step S7 in FIG. 2).

$$(\max)^2 < (SI_k(x))^2 + (CV_k(x))^2 \qquad (1)$$

Then, when the values of the variable max, the ShapeIndex value $SI_k(x)$, and the Curvedness value $CV_k(x)$ do not satisfy the relationship in the Expression (1), the CPU 22 having a function as a shape feature value selecting section continues a process in Step S10 in FIG. 2 described later. Also, when the values of the variable max, the ShapeIndex value $SI_k(x)$, and the Curvedness value $CV_k(x)$ satisfy the relationship in the Expression (1), the CPU 22 having the function as the shape feature value selecting section updates an optimum value $SIp(k)$ of the ShapeIndex value to the value of $SI_k(x)$ calculated in Step S6 in FIG. 2, and updates an optimum value $CVp(k)$ of the Curvedness value to the value of $CV_k(x)$ calculated in Step S6 in FIG. 2 (Step S8 in FIG. 2).

Further, the CPU 22 substitutes the optimum value $SIp(k)$ of the ShapeIndex value and the optimum value $CVp(k)$ of the Curvedness value into the following Expression (2) to calculate the value of the variable max (Step S9 in FIG. 2).

$$\max = \{(SIp(k))^2 + (CVIp(k))^2\}^{1/2} \qquad (2)$$

Then, the CPU 22 determines whether the variable x is N or not (Step S10 in FIG. 2). When the variable x is not N, the CPU 22 adds 1 to the variable x (Step S11 in FIG. 2), and then repeats the processes from Steps S4 to S10 in FIG. 2 described above. When the variable x is N, the CPU 22 sets the optimum value $SIp(k)$ of the ShapeIndex value and the optimum value $CVp(k)$ of the Curvedness value as shape feature values of the voxel corresponding to the pixel k (Step S12 in FIG. 2), and then continues a process in Step S13 in FIG. 2 described later.

The processes from Steps S4 to S9 in FIG. 2 repeated N times in total will be described with reference to FIGS. 3, 4 and 5. The case of N=6 will be hereinafter described by way of example.

The process in Step S4 in FIG. 2 is repeated, and thus as shown in FIG. 4, six local regions $L_k(1)$ to $L_k(6)$ around the pixel k are set in the image in FIG. 3.

In the present embodiment, the N local regions $L_k(x)$ are previously set having different sizes according to the value of the variable x. Specifically, in the case of N=6, for example, the local regions $L_k(x)$ are previously set as regions having sizes of $L_k(1) = A_k(1) \times A_k(1) = 5 \times 5$, $L_k(2) = A_k(2) \times A_k(2) = 7 \times 7$, $L_k(3) = A_k(3) \times A_k(3) = 9 \times 9$, $L_k(4) = A_k(4) \times A_k(4) = 11 \times 11$, $L_k(5) = A_k(5) \times A_k(5) = 13 \times 13$, and $L_k(6) = A_k(6) \times A_k(6) = 15 \times 15$.

Then, the processes in Steps S5 and S6 in FIG. 2 are repeated, and thus ShapeIndex values $SI_k(1)$ to $SI_k(6)$ corresponding to the sizes of the local regions $L_k(1)$ to $L_k(6)$, and the Curvedness values $CV_k(1)$ to $CV_k(6)$ corresponding to the sizes of the local regions $L_k(1)$ to $L_k(6)$ are calculated.

Then, the processes from Steps S7 to S9 in FIG. 2 are repeated, and a set of ShapeIndex value and Curvedness value as optimum values are selected from the six sets of ShapeIndex values and Curvedness values.

Specifically, for example, the six sets of ShapeIndex values and Curvedness values calculated by the processes in Steps S5 and S6 in FIG. 2 exist in coordinate positions as shown in FIG. 5 on a coordinate plane with ShapeIndex value on the abscissa and Curvedness value on the ordinate. At this time, a set of ShapeIndex value and Curvedness value existing in a coordinate position most distant from an original point on the coordinate plane are selected as a shape feature value calculated by an optimum three-dimensional coordinate data amount, specifically, an optimum value SIp(k) of the ShapeIndex value and an optimum values CVp(k) of the Curvedness value. Then, in the case shown in FIG. 5, the ShapeIndex value $SI_k(3)$ is selected as the optimum value SIp(k) of the ShapeIndex value and the Curvedness value $CV_k(3)$ is selected as the optimum value CVp(k) of the Curvedness value.

As described above, the processes from Steps S4 to S9 in FIG. 2 are repeated N times, and thus one local region having an optimum size for calculating a shape feature value used in identifying an elevated shape, that is, an optimum three-dimensional coordinate data amount for calculating the shape feature value is selected from the N local regions. Also, the processes from Steps S4 to S9 in FIG. 2 are repeated N times, and thus a set of ShapeIndex value and Curvedness value as the shape feature value calculated by the optimum three-dimensional coordinate data amount are selected from the N sets of ShapeIndex values and Curvedness values calculated according to the respective N local regions.

Meanwhile, when the CPU 22 determines that the variable x is N in the process in Step S10 in FIG. 2, the CPU 22 further determines whether the processes up to Step S12 in FIG. 2 have been performed for all pixels k (Step S13 in FIG. 2). Then, when the CPU 22 determines that the processes up to Step S12 in FIG. 2 have not been performed for all the pixels k, the CPU 22 sets a next pixel (k+1) (Step S14 in FIG. 2) and then repeats the above-described processes from Steps S3 to S13 in FIG. 2 for the pixel (k+1). When the CPU 22 determines that the processes up to the Step S12 in FIG. 2 have been performed for all the pixels k, the series of processes shown in FIG. 2 performed for one two-dimensional image obtained in Step S1 in FIG. 2 is finished.

Then, the CPU 22 performs a threshold process of each of the optimum value SIp(k) of the ShapeIndex value and the optimum value CVp(k) of the Curvedness value calculated by the series of processes in FIG. 2, and detects a position where a lesion having an elevated shape such as a polyp exists in the two-dimensional image obtained by the process in Step S1 in FIG. 2. Specifically, for example, when a threshold of the ShapeIndex value is SIth and a threshold of the Curvedness value is CVth, the CPU 22 having a function as an elevated shape detecting section detects each pixel from which a shape feature value that satisfies SIp(k)>SIth and CVp(k)>CVth is calculated as a pixel including an image of a lesion having an elevated shape (such as a polyp) in the two-dimensional image obtained by the process in Step S1 in FIG. 2.

As described above, the medical image processing apparatus 3 of the present embodiment can calculate a shape feature value used in identifying an elevated shape according to the size of the elevated shape. Thus, the medical image processing apparatus 3 of the present embodiment can increase detection accuracy in detecting a lesion having an elevated shape in an endoscope image as compared with a conventional apparatus.

The medical image processing apparatus 3 of the present embodiment may perform the series of processes shown in the flowchart in FIG. 2 for one two-dimensional image obtained in Step S1 in FIG. 2, and then further perform a series of processes shown in a flowchart in FIG. 6.

First, the CPU 22 having a function as a pixel extracting section extracts each pixel corresponding to a voxel where CVp(k) is a maximum value from a two-dimensional image having subjected to the process (in FIG. 2), as a pixel corresponding to a vertex of an elevated shape in a three-dimensional model according to the two-dimensional image based on a result of the series of processes in FIG. 2 (Step S21 in FIG. 6). Hereinafter, the case where Q pixels where the CVp (k) is a maximum value are extracted by the process in Step S21 in FIG. 6 will be described. The series of processes described hereinafter is not performed for pixels other than the pixel where the CVp(k) is the maximum value.

Next, the CPU 22 sets a value of one pixel t ($1 \leq t \leq Q$) among the extracted Q pixels to 1 (Step S22 in FIG. 6), and then detects a length $A_t(x)$ of one side in a local region $L_t(x)$ used for calculating SIp(t) and CVp(t) (Step S23 in FIG. 6).

The CPU 22 estimates a size of the local region $L_t(x)$ in a three-dimensional model based on the value of $A_t(x)$ (Step S24 in FIG. 6). Then, the CPU 22 calculates a radius $r_t$ of the elevated shape included in the three-dimensional model of the local region $L_t(x)$ (Step S25 in FIG. 6).

The CPU 22 regards the elevated shape included in the three-dimensional model of the local region $L_t(x)$ as a semi-spherical shape based on the value of the radius $r_t$, and calculates a Curvedness value $CV_t$ in the pixel t using the following Expression (3) (Step S26 in FIG. 6).

$$CV_t = (2(1/r_t)^2)^{1/2} \quad (3)$$

The CPU 22 calculates a correction coefficient $B_t$ for correcting the Curvedness value $CV_t$ based on the value of the radius $r_t$ and a reference radius r using the following Expression (4) (Step S27 in FIG. 6).

$$B_t = r_t / r \quad (4)$$

Then, the CPU 22 having a function as a feature value correcting section calculates a correction value $CV_t(r)$ of the Curvedness value at the pixel t based on the Curvedness value $CV_t$ and the value of the correction coefficient $B_t$ using the following Expression (5) (Step S28 in FIG. 6).

$$CV_t(r) = B_t \times CV_t = (2/r^2)^{1/2} \quad (5)$$

The reference radius r in the Expressions (4) and (5) is a predetermined reference value previously set as a value of a radius of a semispherical three-dimensional model having an ideal shape.

Specifically, the CPU 22 performs the above-described process, and thus calculates Curvedness values at vertexes of elevated shapes having various sizes (various radii) as an identical value using one scale of the reference radius r without depending on the sizes (radii).

Then, the CPU 22 updates an optimum value CVp(t) of the Curvedness value of the voxel corresponding to the pixel t to the value of $CV_t(r)$ calculated in Step S28 in FIG. 6 (from $CV_t(x)$ calculated by the process in FIG. 2) (Step S29 in FIG. 6).

Further, the CPU 22 determines whether the value of the pixel t is Q or not (Step S30 in FIG. 6). When the CPU 22 detects that the value of the pixel t is not Q, the CPU 22 adds 1 to the value of the pixel t (Step S31 in FIG. 6), and then repeats the above-described processes from Steps S23 to S30 in FIG. 6. When the CPU 22 detects that the value of the pixel t is Q, the CPU 22 finishes the series of processes shown in FIGS. 2 and 6 performed for one two-dimensional image obtained in Step S1 in FIG. 2.

Then, the CPU 22 performs a threshold process of each of the optimum value SIp(k) of the ShapeIndex value and the optimum value CVp(k) of the Curvedness value calculated by the series of processes shown in FIGS. 2 and 6, and detects a position where a lesion having an elevated shape such as a polyp exists in the two-dimensional image obtained by the process in Step S1 in FIG. 2. Specifically, for example, when a threshold of the ShapeIndex value is SIth and a threshold of the Curvedness value is CVth, the CPU 22 having a function as an elevated shape detecting section detects each pixel from which a shape feature value that satisfies one of $SIp(k)>SIth$ and $CVp(t)>CVth$, or $SIp(k)>SIth$ and $CVp(k)>CVth$ as a pixel including an image of a lesion having an elevated shape (such as a polyp) in the two-dimensional image obtained by the process in Step S1 in FIG. 2.

As described above, the medical image processing apparatus 3 of the present embodiment performs the series of processes shown in the flowchart in FIG. 2 for one two-dimensional image obtained in Step S1 in FIG. 2, and then performs the series of processes shown in the flowchart in FIG. 6. Thus, the medical image processing apparatus 3 can calculate Curvedness values at vertexes of elevated shapes having various sizes (various radii) as an identical value, and can thereby increase detection accuracy in detecting a lesion having an elevated shape in an endoscope image as compared with a conventional apparatus.

It should be understood that the present invention is not limited to the above-described embodiment, and various changes and applications may be made without departing from the gist of the invention.

What is claimed is:

1. A medical image processing apparatus, comprising:
   a three-dimensional model estimating section that estimates a three-dimensional model of living tissue based on a two-dimensional image of an image of the living tissue inputted from a medical image pickup apparatus;
   a local region setting section that sets a plurality of local regions around a target pixel in the two-dimensional image;
   a shape feature value calculating section that uses three-dimensional coordinate data corresponding to each of the plurality of local regions and calculates shape feature values of respective voxels corresponding to the target pixel based on the three-dimensional model of the living tissue estimated by the three-dimensional model estimating section;
   a shape feature value selecting section that selects, as an optimum shape feature value of a voxel corresponding to the target pixel, a shape feature value calculated according to one local region including an optimum three-dimensional coordinate data amount among the plurality of shape feature values calculated according to the plurality of local regions; and
   an elevated shape detecting section that detects an elevated shape existing in the two-dimensional image based on a selection result of the shape feature value selecting section.

2. The medical image processing apparatus according to claim 1, wherein the shape feature value calculating section calculates at least a first feature value indicating a curvature of a voxel corresponding to the target pixel as the shape feature value.

3. The medical image processing apparatus according to claim 2, wherein the shape feature value calculating section further calculates a second feature value indicating a concave or convex state of the voxel corresponding to the target pixel as the shape feature value.

4. The medical image processing apparatus according to claim 3, wherein the shape feature value selecting section calculates a sum of squares of the first feature value and the second feature value for each of the plurality of shape feature values calculated according to each of the plurality of local regions, and selects a shape feature value at which the sum of squares is maximum as an optimum shape feature value of the voxel corresponding to the target pixel.

5. The medical image processing apparatus according to claim 2, wherein the medical image processing apparatus further comprises:
   a pixel extracting section that extracts each pixel corresponding to a voxel group at which the first feature value is a maximum value in the two-dimensional image; and
   a feature value correcting section that corrects the first feature value in the voxel group corresponding to each pixel using a predetermined reference value in a semi-spherical three-dimensional model having an ideal shape, and
   the elevated shape detecting section detects an elevated shape existing in the two-dimensional image based on the selection result of the shape feature value selecting section and a correction result of the feature value correcting section.

6. The medical image processing apparatus according to claim 3, wherein the medical image processing apparatus further comprises:
   a pixel extracting section that extracts each pixel corresponding to a voxel group at which the first feature value is a maximum value in the two-dimensional image; and
   a feature value correcting section that corrects the first feature value in the voxel group corresponding to each pixel using a predetermined reference value in a semi-spherical three-dimensional model having an ideal shape, and
   the elevated shape detecting section detects an elevated shape existing in the two-dimensional image based on the selection result of the shape feature value selecting section and a correction result of the feature value correcting section.

7. The medical image processing apparatus according to claim 4, wherein the medical image processing apparatus further comprises:
   a pixel extracting section that extracts each pixel corresponding to a voxel group at which the first feature value is a maximum value in the two-dimensional image; and
   a feature value correcting section that corrects the first feature value in the voxel group corresponding to each pixel using a predetermined reference value in a semi-spherical three-dimensional model having an ideal shape, and
   the elevated shape detecting section detects an elevated shape existing in the two-dimensional image based on the selection result of the shape feature value selecting section and a correction result of the feature value correcting section.

8. A medical image processing method, comprising steps of:
   estimating a three-dimensional model of living tissue based on a two-dimensional image of an image of the living tissue inputted from a medical image pickup apparatus;
   setting a plurality of local regions around a target pixel in the two-dimensional image;
   using three-dimensional coordinate data corresponding to each of the plurality of local regions and calculating shape feature values of respective voxels corresponding to the target pixel based on the three-dimensional model of the living tissue;
   selecting, as an optimum shape feature value of a voxel corresponding to the target pixel, a shape feature value calculated according to one local region including an optimum three-dimensional coordinate data amount among the plurality of shape feature values calculated according to the plurality of local regions; and detecting an elevated shape existing in the two-dimensional image based on a result of the selection.

9. The medical image processing method according to claim 8, further comprising a step of calculating at least a first feature value indicating a curvature of a voxel corresponding to the target pixel as the shape feature value of the voxel corresponding to the target pixel.

10. The medical image processing method according to claim 9, further comprising a step of calculating a second feature value indicating a concave or convex state of the voxel corresponding to the target pixel as the shape feature value of the voxel corresponding to the target pixel.

11. The medical image processing method according to claim 10, further comprising a step of calculating a sum of squares of the first feature value and the second feature value for each of the plurality of shape feature values calculated according to each of the plurality of local regions, and selecting a shape feature value at which the sum of squares is maximum as an optimum shape feature value of the voxel corresponding to the target pixel.

12. The medical image processing method according to claim 9, further comprising steps of:

extracting each pixel corresponding to a voxel group at which the first feature value is a maximum value in the two-dimensional image;

correcting the first feature value in the voxel group corresponding to each pixel using a predetermined reference value in a semispherical three-dimensional model having an ideal shape; and detecting an elevated shape existing in the two-dimensional image based on the result of the selection and a result of the correction.

13. The medical image processing method according to claim 10, further comprising steps of:

extracting each pixel corresponding to a voxel group at which the first feature value is a maximum value in the two-dimensional image; and correcting the first feature value in the voxel group corresponding to each pixel using a predetermined reference value in a semispherical three-dimensional model having an ideal shape; and detecting an elevated shape existing in the two-dimensional image based on the result of the selection and a result of the correction.

14. The medical image processing method according to claim 11, further comprising steps of:

extracting each pixel corresponding to a voxel group at which the first feature value is a maximum value in the two-dimensional image; and correcting the first feature value in the voxel group corresponding to each pixel using a predetermined reference value in a semispherical three-dimensional model having an ideal shape, and detecting an elevated shape existing in the two-dimensional image based on the result of the selection and a result of the correction.

* * * * *